US005399337A

United States Patent [19]
Schmitt

[11] Patent Number: 5,399,337
[45] Date of Patent: Mar. 21, 1995

[54] SYNTHESIS OF CRYSTALLINE SUZ-9

[75] Inventor: Kirk D. Schmitt, Pennington, N.J.

[73] Assignee: Mobil Oil Corporation, Fairfax, Va.

[21] Appl. No.: 253,992

[22] Filed: Jun. 3, 1994

[51] Int. Cl.$^6$ ............................................. C01B 33/34
[52] U.S. Cl. ................... 423/705; 423/709; 423/718
[58] Field of Search ............... 423/701, 702, 704, 705, 423/709, 718; 502/62

[56] References Cited

U.S. PATENT DOCUMENTS

| | | | |
|---|---|---|---|
| 3,216,789 | 11/1965 | Breck et al. | 423/718 |
| 3,692,470 | 9/1972 | Ciric | 423/718 |
| 3,950,496 | 4/1976 | Ciric | 423/705 |
| 4,973,461 | 11/1990 | Vaughan | 423/718 |
| 5,350,570 | 9/1994 | Schmitt | 423/701 |

FOREIGN PATENT DOCUMENTS 0526252 2/1993 European Pat. Off. ............ 423/705

OTHER PUBLICATIONS

Lox et al. "The Role of Organic Molecules in Molecular Sieve Synthesis" *Zeolites* (1983) (Oct.) pp. 282–291 vol. 3.

*Primary Examiner*—Mark L. Bell
*Assistant Examiner*—David Sample
*Attorney, Agent, or Firm*—Alexander J. McKillop; Dennis P. Santini

[57] ABSTRACT

This invention relates to a new form of crystalline material identified as having the structure of SUZ-9, to a new and useful method for synthesizing said crystalline material and to use of said crystalline material prepared in accordance herewith as a sorbent or a catalyst for organic compound, e.g., hydrocarbon compound, conversion.

16 Claims, 1 Drawing Sheet

DEGREES TWO-THETA

DEGREES TWO-THETA

SYNTHESIS OF CRYSTALLINE SUZ-9

BACKGROUND OF THE INVENTION

1. Field of the Invention

This invention relates to a new method for synthesizing a highly useful form of crystalline material identified as having the structure of SUZ-9, the new SUZ-9 synthesized, and use of the crystalline material synthesized in accordance herewith as a catalyst component for organic compound, e.g., hydrocarbon compound, conversion, or as a sorbent.

More particularly, this invention relates to a method for preparing the crystalline SUZ-9 structure whereby synthesis is facilitated and reproducible and the product exhibits high purity, improved sorbent properties, and catalytic utility.

2. Discussion of the Prior Art

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of large dimensions, these materials have come to be known as "molecular sieves" and are utilized in a variety of ways to take advantage of these properties.

Such molecular sieves, both natural and synthetic, include a wide variety of positive ion-containing crystalline aluminosilicates. These aluminosilicates can be described as rigid three-dimensional frameworks of $SiO_4$ and $AlO_4$ in which the tetrahedra are crosslinked by the sharing of oxygen atoms whereby the ratio of the total aluminum and silicon atoms to oxygen atoms is 1:2. The electrovalence of the tetrahedra containing aluminum is balanced by the inclusion in the crystal of a cation, for example, an alkali metal or an alkaline earth metal cation. This balanced electrovalence can be expressed by a formula wherein the ratio of aluminum to the number of various cations, such as Ca/2, Sr/2, Na, K, or Li is equal to unity. One type of cation may be exchanged either entirely or partially with another type of cation utilizing ion exchange techniques in a conventional manner. By means of such cation exchange, it has been possible to vary the properties of a given aluminosilicate by suitable selection of the cation. The spaces between the tetrahedra are occupied by molecules of water prior to dehydration.

Prior art techniques have resulted in the formation of a great variety of synthetic zeolites. These zeolites have come to be designated by zeolite A (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); and zeolite ZSM-12 (U.S. Pat. No. 3,832,449), merely to name a few.

Although the term "zeolites" encompasses materials containing silica and alumina, it is recognized that the silica and alumina portions may be replaced in whole or in part with other oxides. More particularly, $GeO_2$ is an art-recognized substitute for $SiO_2$. Also, $B_2O_3$, $Cr_2O_3$, $Fe_2O_3$, and $Ga_2O_3$ are art-recognized replacements for $Al_2O_3$. Accordingly, the term "zeolite" as used herein shall connote not only materials containing silicon and, optionally, aluminum atoms in the crystalline lattice structure thereof, but also materials which contain suitable replacement atoms for such silicon and/or aluminum. On the other hand, the term "aluminosilicate zeolite" as used herein shall define zeolite materials consisting essentially of silicon and aluminum atoms in the crystalline lattice structure thereof, as opposed to materials which contain substantial amounts of suitable replacement atoms for such silicon and/or aluminum.

Although certain zeolites can be prepared from totally inorganic reaction mixtures, the synthesis of other zeolites is often promoted or made possible by the inclusion of certain organic compounds, termed "organic directing agents", in the reaction mixture. Note the article by Lok et al., "The Role of Organic Molecules in Molecular Sieve Synthesis," *Zeolites* 3, 282–291 (1983). When such organic directing agents are used, they may be included in an aqueous reaction mixture containing reactants, e.g., sources of silica and alumina, necessary for the zeolite synthesis. The reaction mixture may then be maintained under sufficient conditions, e.g., at elevated temperature, until the desired crystals are formed. These crystals may then be recovered by filtration and washing the filtered crystals with water. This filtering and washing treatment separates the crystals from organic directing agent which is either included in the mother liquor of the reaction mixture or loosely associated with the exterior surface of the crystals. However, a residue of the organic directing agent, e.g., amines and especially quaternary ammonium compounds, usually remains more tenaciously attached to the zeolite crystals. This tenaciously-attached residue, which is not removed by the filtering and washing treatment, may be occluded within the pores of the zeolite and/or firmly affixed to the surface of the zeolite. Certain residues which are tenaciously attached to the zeolite may occupy cation exchange sites of the zeolite, especially in the case of quaternary ammonium residues. It is particularly important to remove organic residue which occludes in the pores of the zeolite because this type of residue may constitute obstructions which tend to substantially reduce the sorption capacity and catalytic activity of the zeolite.

In order to remove the residue of organic directing agents from as-synthesized zeolites, which residue cannot be readily removed by filtration and washing, the zeolite, so long as it is stable under the conditions, may be calcined at elevated temperatures, such as about 400° C. or higher, in the presence of a source of oxygen such as air for at least one hour. This calcination treatment promotes the decomposition and/or volatilization of the residue. The presence of oxygen during the calcination further promotes oxidation, e.g., combustion, of the organic residue into oxidized species, e.g., carbon dioxide, carbon monoxide, water, and nitrogen oxides, which are evolved as gases.

Conventional synthesis of SUZ-9 is taught in European Patent Application 526,252, entirely incorporated herein by reference. The synthesis comprises heating an aqueous reaction mixture under alkaline conditions containing sources of alkali metal oxide, aluminum oxide, silicon oxide, organic directing agent, and water. The organic directing agent is 1,3,4,6,7,9-hexahydro-2,2,5,5,8,8-hexamethyl-2H-benzo((1,2-C:3,5-C':5,6-

C''')tripyrolium trihydroxide or halide, or its precursor or reaction product, referred to as the tripyrolium compound, and, preferably, tetraethylammonium hydroxide or halide or its precursor or reaction product. The tripyrolium compound is identified in U.S. Pat. No. 3,950,496, incorporated herein by reference, for use as directing agent in synthesis of ZSM-18. The structure of the tripyrolium cation, referred to as "trisquat" in EPA 526,252, may be represented as follows:

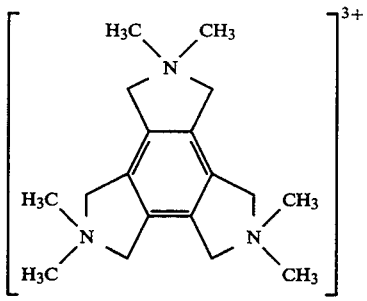
(1)

Applicant knows of no prior art method for preparing a crystalline structure identified as SUZ-9 utilizing the present method.

SUMMARY OF THE INVENTION

An economical and reproducible method for preparing stable crystalline material identified as SUZ-9 exhibiting high catalytic activity and other valuable properties is provided. The method comprises forming a reaction mixture hydrogel containing sources of alkali metal (M) cations, e.g., potassium or sodium; an oxide of trivalent element (X), e.g., aluminum, boron, iron, gallium, indium and mixtures thereof; an oxide of tetravalent element (Y), e.g., silicon, germanium, tin and mixtures thereof; an organic directing agent (R), more particularly described as triquat (2) hereinafter; and water, said reaction mixture having a composition in terms of mole ratios, within the following ranges:

| Reactants | Useful | Preferred |
| --- | --- | --- |
| $YO_2/X_2O_3$ | 8 to 30 | 9 to 20 |
| $H_2O/YO_2$ | 8 to 22 | 10 to 18 |
| $OH^-/YO_2$ | 0.4 to 1.1 | 0.5 to 1.0 |
| $M/YO_2$ | 0.2 to 1.3 | 0.4 to 1.0 |
| $R/YO_2$ | 0.03 to 1.2 | 0.04 to 1.0 |

The method further comprises maintaining the reaction mixture until crystals of SUZ-9 structure are formed. Reaction conditions required consist of heating the foregoing reaction mixture to a temperature of from about 110° C. to about 150° C. for a period of time of from about 40 hours to about 10 days. A more preferred temperature range is from about 130° C. to about 140° C. with the amount of time at a temperature in such range being from about 80 hours to about 5 days. The solid product comprising SUZ-9 crystals is recovered from the reaction medium, as by cooling the whole to room temperature, filtering and water washing.

EMBODIMENTS

Figure 1:
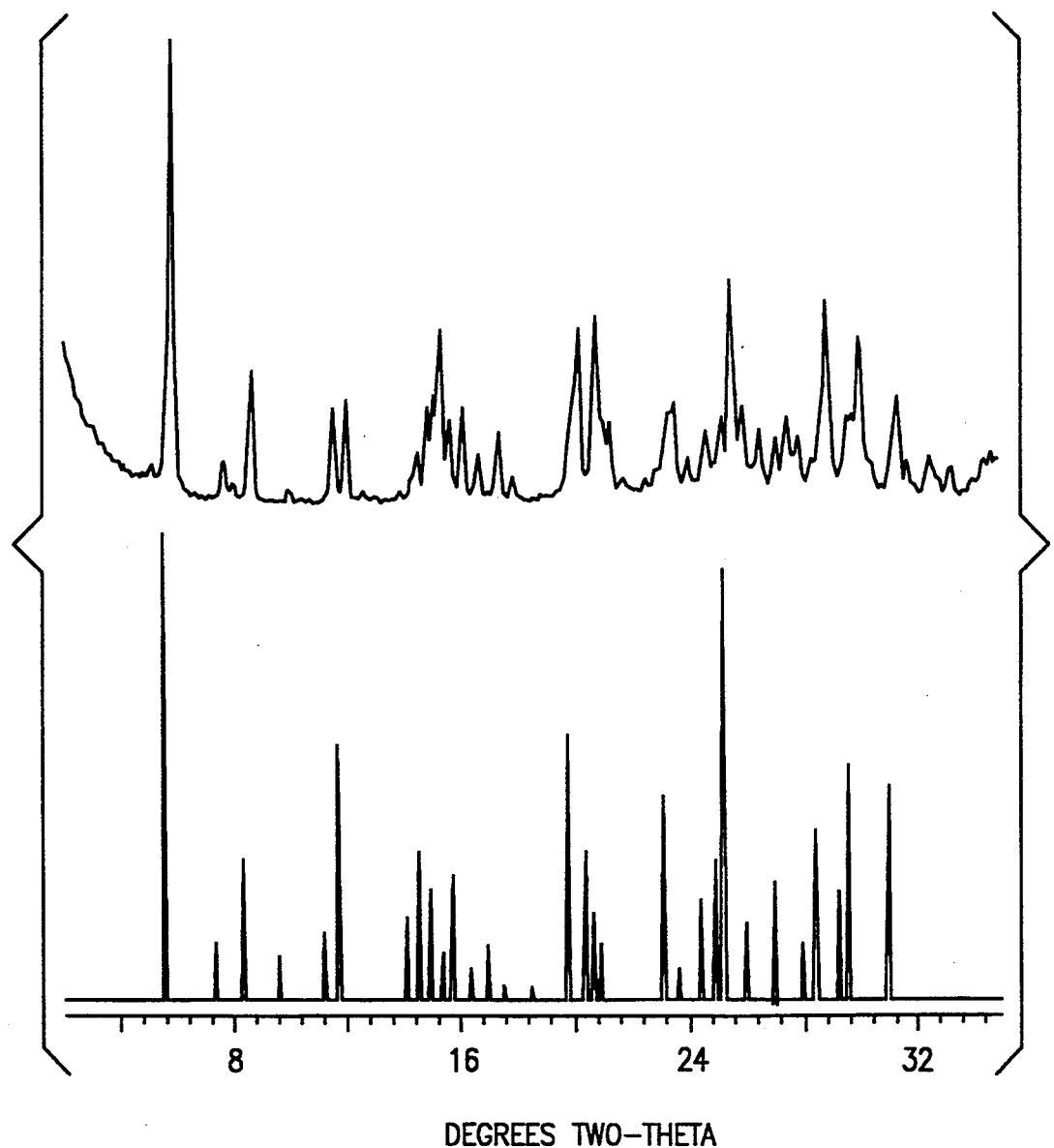
FIG. 1 shows the X-ray pattern for the product of Example 1.

The different triquat directing agent (R) required for use herein has a formula $C_{15}H_{39}N_4^{+++}$, and may be represented as follows:

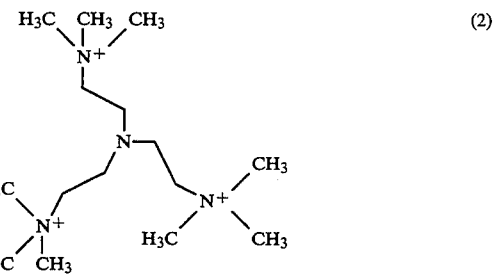
(2)

The source of the directing agent may be, for example, the halide, e.g., chloride or bromide, salt. Triquat (2) was synthesized for use herein, as follows:

A 500 mL Parr autoclave was charged with 25 g $(ClCH_2CH_2)_3N \cdot HCl$ (Aldrich) and 250 mL MeOH, sealed, cooled in Dry Ice and evacuated to <2 Torr when 50 g $Me_3N$ (anhydrous gas, Aldrich) were run in from an inverted cylinder. The mixture was warmed to room temperature in a water bath, then at 5° C./minute to 92° C., held 7 hours at 92° C., cooled to room temperature, filtered and stripped to give a white paste. The yield of tris-quaternary at this point was 100% with no impurities visible to C-nmr except that the HCl in the original salt had trapped one mole/mole of $Me_3N$ as its hydrochloride. The product was dissolved in 700 mL $H_2O$, eluted over 1 hour through 700 mL IRA-100 anion exchange resin and stripped to about 200 mL on a rotary evaporator. Stripping removed the $Me_3N$. Generally, enough $H_2O$ was stripped to give a 1.15–1.3N (0.38–0.43M in triquat (2)) solution. Titration of the base gave 94–98% yield of a product whose C-nmr showed only the expected peaks at 64.7 (triplet), 55.7 (triplet), and 48.9 vs. DSS in $D_2O$. The product was crystallized from water in low yield as the tetradecahydrate as indicated by elemental analysis and proton nmr.

The particular effectiveness of the presently required organic directing agent, i.e., triquat (2), when compared with any other directing agent, except for the tripyrolium trisquat cation (1) above, for the present synthesis is believed due to its ability to function as a template in the nucleation and growth of SUZ-9 crystals from the above reaction mixture. This is true even though no predigestion of the gel is required prior to crystallization. This different organic agent functions in this fashion in the reaction mixture having the above described composition and under the above described conditions of temperature and time.

It should be noted that the ratio of components of the reaction mixture required herein are critical to achieve maximum effectiveness. For instance, if the $YO_2/X_2O_3$ mole ratio, e.g., $SiO_2/Al_2O_3$ ratio, is too high or the ratio of tetraethylammonium to triquat (2) is too high, something other than SUZ-9 crystal will form. Still further, for most effective synthesis of SUZ-9 by this method, the reaction temperature should be maintained within the range of from about 110° C. to about 150° C., preferably from about 130° C. to about 140° C.

The synthesis of the present invention is facilitated when the reaction mixture comprises seed crystals, such as those having the structure of SUZ-9. The use of at least 0.01%, preferably about 0.10%, and even more preferably about 1% seed crystals (based on total weight) of crystalline material will be useful.

The reaction mixture composition for the synthesis of SUZ-9 crystals hereby can be prepared utilizing materials which can supply the appropriate oxide. The useful sources of $X_2O_3$, e.g., aluminum oxide, iron oxide and/or boron oxide, include, as non-limiting examples, any known form of such oxide, e.g., aluminum oxide or hydroxide, organic or inorganic salt or compound, e.g., alumina, aluminates and borates. The useful sources of $YO_2$, e.g., silicon oxide, include, as non-limiting examples, known forms of such oxide, e.g., silicic acid or silicon dioxide, alkoxy- or other compounds of silicon, including silica gel and silica hydrosol.

It will be understood that each oxide component utilized in the reaction mixture for this synthesis can be supplied by one or more essential reactants and they can be mixed together in any order. For example, any oxide can be supplied by an aqueous solution. The reaction mixture can be prepared either batchwise or continuously. Crystal size and crystallization time for the product composition comprising the SUZ-9 crystals may vary somewhat with the exact nature of the reaction mixture employed within the above limitations.

The calcined SUZ-9 crystal composition prepared hereby has a characteristic X-ray diffraction pattern, including values substantially as set forth in Table I, hereinafter.

TABLE I

| Interplanar d-Spacing, (A) | Relative Intensity (I/I$_o$) |
|---|---|
| 15.66 ± 0.30 | VS |
| 11.89 ± 0.25 | W |
| 10.46 ± 0.25 | M |
| 9.04 ± 0.15 | VW |
| 7.85 ± 0.15 | M |
| 7.55 ± 0.15 | M/S |
| 6.97 ± 0.15 | VW |
| 6.32 ± 0.12 | W/M |
| 6.13 ± 0.12 | M/S |
| 5.92 ± 0.12 | S |
| 5.80 ± 0.12 | M |
| 5.63 ± 0.12 | M |
| 5.44 ± 0.12 | W/M |
| 5.22 ± 0.12 | M |
| 5.07 ± 0.12 | VW/W |
| 4.48 ± 0.10 | S |
| 4.35 ± 0.10 | S |
| 4.26 ± 0.10 | M/S |
| 3.86 ± 0.08 | M |
| 3.78 ± 0.08 | W/M |
| 3.67 ± 0.08 | W/M |
| 3.60 ± 0.08 | M/S |
| 3.55 ± 0.08 | VS |
| 3.49 ± 0.07 | W/M |
| 3.42 ± 0.07 | W/M |
| 3.35 ± 0.07 | M |
| 3.30 ± 0.07 | M |
| 3.25 ± 0.07 | W/M |
| 3.21 ± 0.07 | W/M |
| 3.14 ± 0.07 | S |
| 3.06 ± 0.07 | M |
| 3.02 ± 0.07 | S |
| 2.89 ± 0.06 | M/S |
| 2.86 ± 0.06 | W |
| 2.78 ± 0.06 | W |
| 2.73 ± 0.06 | VW/W |
| 2.64 ± 0.06 | VW/W |
| 2.59 ± 0.06 | W/M |
| 2.52 ± 0.06 | VW/W |

These X-ray diffraction data were collected with a Scintag theta-theta powder diffraction system, equipped with a graphite diffracted beam monochromator and scintillation counter, using copper K-alpha radiation. The diffraction data were recorded by step-scanning at 0.04 degrees of two-theta, where theta is the Bragg angle, and a counting time of 1 second for each step. The interplanar spacings, d's, were calculated in Angstrom units (A), and the relative intensities of the lines, I/I$_o$, where I$_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols VS=very strong (60–100), S=strong (40–60), M=medium (20–40), W=weak (10–20) and VW=very weak (0–10). It should be understood that diffraction data listed for this sample as single lines may consist of multiple overlapping lines which under certain conditions, such as differences in crystallite sizes or very high experimental resolution or crystallographic change, may appear as resolved or partially resolved lines. Typically, crystallographic changes can include minor changes in unit cell parameters and/or a change in crystal symmetry, without a change in topology of the structure. These minor effects, including changes in relative intensities, can also occur as a result of differences in cation content, framework composition, nature and degree of pore filling, and thermal and/or hydrothermal history.

X-ray diffraction data were also collected on a synchrotron beamline at the National Synchrotron Light Source at Brookhaven, N.Y.

The crystalline SUZ-9 prepared hereby has a composition involving the molar relationship:

$$X_2O_3: (y) YO_2$$

wherein X is a trivalent element, such as aluminum, boron, iron, indium and/or gallium, preferably aluminum; Y is a tetravalent element, such as silicon, tin and/or germanium, preferably silicon; and y is from about 4 to about 8, usually from about 5 to about 7. Any M and R components associated with the as-synthesized material as a result of their presence during crystallization are easily removed by post-crystallization methods hereinafter more particularly described.

Reasons for little having been accomplished with SUZ-9 include the need, until the present invention, for one specific organic directing agent or, preferably, directing agent combination to synthesize it, i.e., tripyrolium trisquat (1) above, or, preferably, trisquat (1) with tetraethyl-ammonium added, and the complexity and cost of tripyrolium trisquat (1) manufacture. Synthesis of tripyrolium trisquat (1) is complex, with low yields, and has a photochemical bromination step if the bromide is desired. See *J. Am. Chem. Soc.*, 100, 2173–2175 (1978).

The present invention provides an SUZ-9 synthesis with distinct advantages over that taught by European Patent Application 526,252, referred to above. First, triquat (2) is easy to manufacture in large quantities. It is available in a one-step synthesis from a fine chemical, i.e., tris(chloroethylamine)hydrochloride, as follows:

$$(ClCH_2CH_2)_3N.HCl + Me_3N \rightarrow$$
$$(Me_3N^+CH_2CH_2)_3N$$

Tris(choroethylamine) hydrochloride is available from commodity chemicals as follows:

$$N(CH_2CH_2OH)_3 + SOCl_2 \rightarrow (ClCH_2CH_2)_3N.HCl$$

Second, triquat (2) may be easily and routinely removed from the SUZ-9 structure to form the porous, hydrogen-form of the zeolite necessary for catalytic applications.

Third, no supplemental organic, e.g., tetraethylammonium hydroxide or halide, is needed for synthesis of pure SUZ-9 by the present invention.

Synthetic SUZ-9 crystals prepared in accordance herewith can be used in the hydrogen form or another univalent or multivalent cationic form. It can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such components can be exchanged into the composition, impregnated therein or physically intimately admixed therewith. Such components can be impregnated in or on to the SUZ-9 such as, for example, by, in the case of platinum, treating the material with a platinum metal-containing ion. Suitable platinum compounds for this purpose include chloroplatinic acid, platinum chloride and various compounds containing the platinum amine complex. Combinations of metals and methods for their introduction can also be used.

Synthetic SUZ-9 crystals, when employed either as an adsorbent or as a catalyst in a hydrocarbon conversion process, should be dehydrated at least partially. This can be done by heating to a temperature in the range of from about 65° C. to about 315° C. in an inert atmosphere, such as air, nitrogen, etc., and at atmospheric or subatmospheric pressures for between 1 and 48 hours. Dehydration can be performed at lower temperature merely by placing the zeolite in a vacuum, but a longer time is required to obtain a particular degree of dehydration. The crystalline thermal decomposition product of the newly synthesized SUZ-9 can be prepared by heating same at a temperature of from about 200° C. to about 550° C. for from 1 hour to about 48 hours.

The original cations, e.g., alkali metal, of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which render the material catalytically active, especially for certain hydrocarbon conversion reactions. These include hydrogen, rare earth metals and metals of Groups IIA, IIIA, IVA, IB, IIB, IIIB, IVB, and VIII of the Periodic Table of the Elements, especially gallium, indium, and tin.

Typical ion exchange technique would be to contact the synthetic SUZ-9 material with a salt of the desired replacing cation or cations. Examples of such salts include the halides, e.g., chlorides, nitrates and sulfates.

Representative ion exchange techniques are disclosed in a wide variety of patents including U.S. Pat. Nos. 3,140,249; 3,140,251; and 3,140,253.

Following contact with the salt solution of the desired replacing cation, the SUZ-9 is then preferably washed with water and dried at a temperature ranging from 65° C. to about 315° C. and thereafter may be calcined in air or other inert gas at temperatures ranging from about 200° C. to about 550° C. for periods of time ranging from 1 to 48 hours or more to produce a catalytically-active crystalline thermal decomposition product thereof.

The crystalline SUZ-9 prepared by the instant invention is formed in a wide variety of particle sizes. Generally speaking, the particles can be in the form of a powder, a granule, or a molded product, such as extrudate having particle size sufficient to pass through a 2 mesh (Tyler) screen and be retained on a 400 mesh (Tyler) screen. In cases where the catalyst is molded, such as by extrusion, the crystalline material can be extruded before drying or dried or partially dried and then extruded.

In the case of many catalysts, it is desired to incorporate the crystals hereby prepared with another material resistant to the temperatures and other conditions employed in certain organic conversion processes. Such matrix materials include active and inactive materials and synthetic or naturally occurring zeolites as well as inorganic materials such as clays, silica and/or metal oxides, e.g., alumina, titania and/or zirconia. The latter may be either naturally occurring or in the form of gelatinous precipitates, sols or gels including mixtures of silica and metal oxides. Use of a material in conjunction with the SUZ-9, i.e., combined therewith, which is active, may enhance the conversion and/or selectivity of the catalyst in certain organic conversion processes. Inactive materials suitably serve as diluents to control the amount of conversion in a given process so that products can be obtained economically and orderly without employing other means for controlling the rate or reaction. Frequently, crystalline catalytic materials have been incorporated into naturally occurring clays, e.g., bentonite and kaolin. These materials, i.e., clays, oxides, etc., function, in part, as binders for the catalyst. It is desirable to provide a catalyst having good crush strength because in a petroleum refinery the catalyst is often subjected to rough handling, which tends to break the catalyst down into powder-like materials which cause problems in processing.

Naturally occurring clays which can be composited with the hereby synthesized crystalline material include the montmorillonite and kaolin families which include the subbentonites, and the kaolins commonly known as Dixie, McNamee, Georgia and Florida clays, or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the present crystals can be composited with a porous matrix material such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. The matrix can be in the form of a cogel. A mixture of these components could also be used.

The relative proportions of finely divided crystalline material and matrix vary widely with the crystalline material content ranging from about 1 to about 90 percent by weight, and more usually in the range of about 2 to about 50 percent by weight of the composite.

Employing a catalytically active form of the catalyst of this invention which may contain additional hydrogenation components, reforming stocks can be reformed employing a temperature between about 370° C. and about 540° C. The pressure can be between about 100 psig and about 1000 psig, but it is preferably between about 200 psig and about 700 psig. The liquid hourly space velocity is generally between about 0.1 and about 10 hr$^{-1}$, preferably between about 0.5 and about 4 hr$^{-1}$, and the hydrogen to hydrocarbon mole ratio is generally between about 1 and about 20, preferably between about 4 and about 12.

The catalyst can also be used for hydroisomerization of normal paraffins, when provided with a hydrogenation component, e.g., platinum. Hydroisomerization is carried out at a temperature between about 90° C. and 375° C., preferably about 145° C. to about 290° C., with a liquid hourly space velocity between about 0.01 and about 2 hr$^{-1}$ preferably between about 0.25 and about 0.50 hr$^{-1}$ employing hydrogen such that the hydrogen to hydrocarbon mole ratio is between about 1:1 and about 5:1.

The catalyst can also be used for reducing the pour point of gas oils. This reaction may be conducted at a liquid hourly space velocity between about 10 and about 30 hr$^{-1}$ and at a temperature between about 400° C. and about 540° C.

Other reactions which can be accomplished employing the SUZ-9 catalyst of this invention containing a metal, e.g., platinum, include hydrogenation-dehydrogenation reactions and desulfurization reactions. The new and improved SUZ-9 of the present invention will perform as a sorbent or catalyst for all the processes disclosed for SUZ-9 use in European Patent Application 526,252, incorporated in its entirety herein by reference.

In order to more fully illustrate the nature of the invention and the manner of practicing same, the following examples are presented. When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec$^{-1}$). The Alpha Test is described in U.S. Pat. No. 3,354,078; in the *Journal of Catalysis*, vol. 4, 527 (1965); vol. 6, 278 (1966); and vol. 61, 395 (1980), each incorporated herein by reference as to that description. The experimental conditions of the test used herein include a constant temperature of 538° C. and a variable flow rate as described in detail in the *Journal of Catalysis*, vol. 61, 395.

EXAMPLE 1

This preparation was essentially identical to Example 5 of EPA 526,252 except that triquat ion (2) was substituted for the tripyrolium trisquat (1). To a solution of 4.11 g KOH and 15.8 mL 1.83N triquat (2) hydroxide prepared above were added 9.5 g Cabosil fumed silica. Simultaneously 2.6 g sodium aluminate were dissolved in 20.2 mL H$_2$O. When the sodium aluminate has all dissolved, the two solutions were mixed, stirred magnetically for 3 hours at room temperature, sealed in a stainless steel reactor, and heated for 93 hours at 135° C. without stirring. The product was centrifuged, washed twice with 100 mL H$_2$O, and dried overnight at 85° C. to give 6.7 g product.

The product was calcined by heating 3° C./minute to 500° C. under flowing N$_2$, holding for 3 hours at 500° C., cooling to 250° C., heating 3° C./minute to 500° C. under flowing air, holding for 6 hours at 500° C., and cooling under N$_2$. This product was exchanged 3 times with 20 mL/g 1M NH$_4$Cl (pH adjusted to 8.0 with NH$_4$OH) and recalcined 3° C./minute to 500° C. under flowing air and holding for 3 hours at 500° C. before cooling.

The product calcined SUZ-9 was analyzed by X-ray diffraction and found to exhibit the pattern shown in FIG. 1. In FIG. 1, the actual Scintag X-ray data for the product of this example is presented at the top of the Figure. A simulation of peak positions and intensities from the values of Table I is presented at the bottom of FIG. 1 for comparison.

EXAMPLE 2

This preparation was essentially identical to Example 2 of EPA 526,252 except that triquat ion (2) was substituted for tripyrolium trisquat (1) and a vertical stirring shaft was used instead of revolving the pressure vessel. To a solution of 5.71 g KOH, 14.4 mL 1.83N triquat (2) hydroxide, and 34.9 g 25% tetraethylammonium hydroxide were added 14.2 g Cabosil fumed silica. Simultaneously 3.0 g sodium aluminate were dissolved in 20 mL H$_2$O. The solutions were mixed and stirred magnetically, then sealed in a 300 mL Parr reactor with 3 blades set to sweep the entire depth of the solution. The mixture was stirred 8–10 rpm, heated 2° C./minute to 135° C., and held at that temperature for 116 hours. The recovered solid product was calcined, NH$_4$Cl exchanged, and recalcined as described in Example 1.

The product calcined SUZ-9 was analyzed by X-ray diffraction on the synchrotron beamline and found to be essentially pure SUZ-9 exhibiting the X-ray data of Table II.

TABLE II

| Interplanar d-spacing (A) | Relative Intensity |
| --- | --- |
| 32.23 | VW |
| 18.10 | VW |
| 15.68 | VS |
| 11.84 | W |
| 11.35 | W |
| 10.44 | M |
| 9.04 | VW |
| 7.84 | VW |
| 7.81 | VW |
| 7.54 | W |
| 6.96 | VW |
| 6.35 | VW |
| 6.26 | VW |
| 6.11 | W |
| 6.02 | W |
| 5.91 | M |
| 5.79 | VW |
| 5.62 | W |
| 5.43 | W |
| 5.21 | VW |
| 5.20 | VW |
| 5.06 | VW |
| 4.52 | VW |
| 4.51 | VW |
| 4.47 | M |
| 4.34 | M |
| 4.29 | VW |
| 4.25 | W |
| 3.87 | VW |
| 3.84 | W |
| 3.66 | VW |
| 3.59 | W |
| 3.55 | M |
| 3.50 | VW |
| 3.41 | W |
| 3.34 | W |
| 3.30 | W |
| 3.25 | VW |
| 3.19 | VW |
| 3.13 | M |
| 3.06 | VW |

TABLE II-continued

| Interplanar d-spacing (A) | Relative Intensity |
| --- | --- |
| 3.01 | M |

EXAMPLE 3

The product of Example 2 was evaluated for sorption of n-hexane at 40 Torr and 25° C. to compare with the sorption result reported for the Example 2 product of EPA 526,252. The presently prepared SUZ-9 had an n-hexane sorption capacity of 10.6%, compared to the reported n-hexane sorption capacity of the prior art preparation of SUZ-9 of 6.8% at 80 Torr and 25° C. The sorption of SUZ-9 made by the present invention is thus at least 50% greater than that claimed in EPA 526,252. Note that sorption increases with pressure and the maximum pressure used herein was less than that in the reference. The higher sorption may indicate either that use of the present template makes a purer product, or that less crystallinity loss occurs during calcination, or both.

EXAMPLE 4

A sample of the product of Example 2 was subjected to the Alpha Test and found to have an Alpha Value of 43. This value aged to 35 after 1 hour at 530° C. under standard conditions.

Changes and modifications in the specifically described embodiments can be carried out without departing from the scope of the invention which is intended to be limited only by the scope of the appended claims.

What is claimed is:

1. A method for synthesizing crystalline material exhibiting a characteristic X-ray diffraction pattern including d-spacing maxima values as shown in Table I, which comprises (i) preparing a mixture capable of forming said material, said mixture comprising sources of alkali metal (M), an oxide of trivalent element (X), an oxide of tetravalent element (Y), water and triquat (R) having a formula $C_{15}H_{39}N_4^{+++}$ and represented as follows:

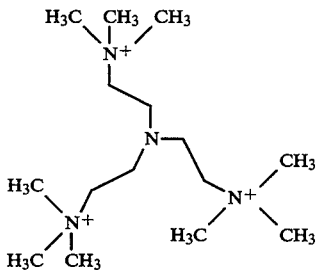

and having a composition, in terms of mole ratios, within the following ranges:

| $YO_2/X_2O_2$ | 8 to 30 |
| --- | --- |
| $H_2O/YO_2$ | 8 to 22 |
| $OH^-/YO_2$ | 0.4 to 1.1 |
| $M/YO_2$ | 0.2 to 1.3 |
| $R/YO_2$ | 0.03 to 1.2 |

(ii) maintaining said mixture under sufficient conditions including a temperature of from about 110° C. to about 150° C. until crystals of said material are formed; and (iii) recovering said crystalline material from step (ii), said recovered crystalline material containing said R.

2. The method of claim 1 wherein said mixture has the following composition ranges:

| $YO_2/X_2O_3$ | 9 to 20 |
| --- | --- |
| $H_2O/YO_2$ | 10 to 18 |
| $OH^-/YO_2$ | 0.5 to 1.0 |
| $M/YO_2$ | 0.4 to 1.0 |
| $R/YO_2$ | 0.04 to 1.0. |

3. The method of claim 1 wherein said mixture further comprises seed crystals in sufficient amount to enhance synthesis of said crystalline material.

4. The method of claim 1 wherein said X is aluminum, boron, iron, gallium, indium or a mixture thereof, and said Y is silicon, germanium, tin or a mixture thereof.

5. The method of claim 1 wherein X comprises aluminum and Y comprises silicon.

6. The method of claim 1 comprising replacing ions of the crystalline material recovered in step (iii), at least in part, by ion exchange with an ion or a mixture of ions selected from the group consisting of hydrogen and hydrogen precursors, rare earth metals and metals from Groups IIA, IIIA, IVA, IB, IIB, IIIB, IVB, VIB and VIII of the Periodic Table of Elements.

7. The method of claim 2 comprising replacing ions of the crystalline material recovered in step (iii), at least in part, by ion exchange with an ion or a mixture of ions selected from the group consisting of hydrogen and hydrogen precursors, rare earth metals and metals from Groups IIA, IIIA, IVA, IB, IIB, IIIB, IVB, VIB and VIII of the Periodic Table of Elements.

8. The method of claim 6 wherein said replacing ion is hydrogen or a hydrogen precursor.

9. The method of claim 7 wherein said replacing ion is hydrogen or a hydrogen precursor.

10. The recovered crystalline material of claim 1.

11. The recovered crystalline material of claim 2.

12. The R-containing product crystalline material of claim 6.

13. The R-containing product crystalline material of claim 7.

14. The R-containing product crystalline material of claim 8.

15. The R-containing product crystalline material of claim 9.

16. A mixture capable of forming crystals of SUZ-9 upon crystallization, said mixture comprising sources of alkali metal (M), trivalent element (X) oxide selected from the group consisting of oxide of aluminum, boron, iron, gallium, indium and mixtures thereof; tetravalent element (Y) oxide selected from the group consisting of oxide of silicon, germanium, tin and mixtures thereof; water and triquat (R) having the formula $C_{15}H_{39}N_4^{+++}$, represented as follows:

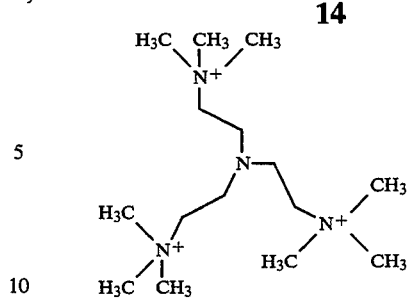
and having a composition, in terms of mole ratios, within the following ranges:
| | |
|---|---|
| $YO_2/X_2O_3$ | 8 to 30 |
| $H_2O/YO_2$ | 8 to 22 |
| $OH^-/YO_2$ | 0.4 to 1.1 |
| $M/YO_2$ | 0.2 to 1.3 |
| $R/YO_2$ | 0.03 to 1.2. |
* * * * *